United States Patent [19]

Steinman

[11] 4,070,369

[45] * Jan. 24, 1978

[54] 2-AMINOMETHYL-5-CHLORO-3-(2,4-DICHLOROPHENYL)INDOLE

[75] Inventor: Martin Steinman, Livingston, N.J.

[73] Assignee: Schering Corporation, Kenilworth, N.J.

[*] Notice: The portion of the term of this patent subsequent to Mar. 16, 1993, has been disclaimed.

[21] Appl. No.: 715,598

[22] Filed: Aug. 18, 1976

Related U.S. Application Data

[60] Continuation-in-part of Ser. No. 636,517, Dec. 1, 1975, Pat. No. 3,996,159, which is a division of Ser. No. 473,625, May 28, 1974, Pat. No. 3,944,672, which is a continuation-in-part of Ser. No. 314,899, Dec. 13, 1972, abandoned.

[51] Int. Cl.$^2$ .......................................... C07D 209/14
[52] U.S. Cl. ..................... 260/326.15; 260/319.1; 260/465 E
[58] Field of Search ................................. 260/326.15

[56] References Cited

U.S. PATENT DOCUMENTS 3,723,461   3/1973   Yamamoto et al. ............ 260/326.15

FOREIGN PATENT DOCUMENTS 1,446,093   8/1976   United Kingdom ............ 260/326.15

Primary Examiner—Ethel G. Love
Attorney, Agent, or Firm—Barbara L. Cowley Renda; Stephen B. Coan; Bruce M. Eisen

[57] ABSTRACT

Disclosed herein is the novel compound, 2-aminomethyl-5-chloro-3-(2,4-dichlorophenyl)indole, useful by virtue of its antimicrobial, sanitizing, disinfectant, preservative, viricidal and herbicidal properties.

1 Claim, No Drawings

2-AMINOMETHYL-5-CHLORO-3-(2,4-DICHLOROPHENYL)INDOLE

This application is a continuation-in-part of my copending application Ser. No. 636,517 filed Dec. 1, 1975, and now U.S. Pat. No. 3,996,159 issued Dec. 7, 1976; which in turn is a division of application Ser. No. 473,625, filed May 28, 1974 and now U.S. Pat. No. 3,944,672; which is a continuation-in-part of application Ser. No. 314,899, filed Dec. 13, 1972, and now abandoned.

The present invention relates to 2-aminomethyl-5-chloro-3-(2,4-dichlorophenyl)indole and its acid addition salts which are useful as antimicrobial agents, preservatives and viricides. Most particularly, this invention relates to a compound of the formula:

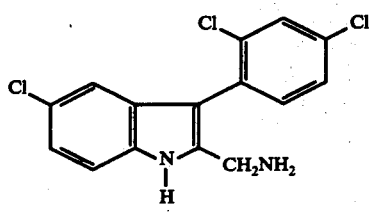

(I)

and the acid addition salts thereof.

The acid addition salts are more convenient to use in certain applications; for example, their convenient physical properties such as crystalline form or solubility are advantageous over the free base in certain types of formulations. When the salts are used in a pharmaceutical or edible preparation, the anion must, of course, be substantially non-toxic at the concentration or dosage used; when the salts are used in technical fields such as the preservation of paper, leather, or photographic goods the anion need not necessarily be non-toxic.

Suitable acid addition salts of the compound of formula I may be derived from a variety of inorganic and organic acids such as sulfuric, phosphoric, hydrochloric, hydrobromic, acetic, malic, maleic, succinic, tartaric, cinnamic, citric, phthalic, ascorbic and other related acids.

The 2-aminomethyl-3-(2,4-dichlorophenyl)indole of formula I and its acid addition salts can be prepared by standard methods known for the preparation of substituted indoles or of amines; for example, by the processes described in U.S. Pat. Nos. 3,697,508; 3,558,604 and 3,558,603; Belgian Pat. No. 724,993; and Inaba, Ishizumi and Yamamoto, Chem. Pharm. Bull., 19 (2), 263–272 (1971).

A convenient synthetic route for the 3-phenylindole nucleus involves the formation of N-[2-(2,4-dichlorobenzoyl)-4-chloro]phenylglycinonitrile from 2-amino-2', 4', 5-trichlorobenzophenone and further conversion of this intermediate to 5-chloro-3-(2,4-dichlorophenyl)indole-2-carbonitrile.

The 3-phenylindole nucleus itself may also be obtained by a Fischer indole synthesis, or by an equivalent reaction in which a benzenediazonium salt reacts with an ester of a 2-benzylacetoacetic acid in the presence of alkali and the product is cyclized by heating in the presence of acid or in ethylene glycol. Further modifications, especially transformation of the substituent at the 2-position, and/or removal of a blocking or protecting group at the 1-position, may then be effected.

Typical final steps are reduction of the precursor compound of the formula:

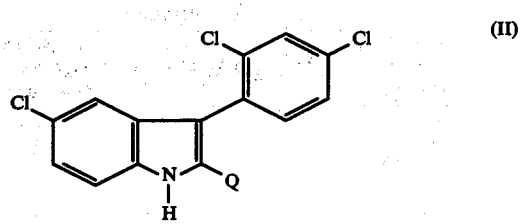

(II)

wherein Q is a group directly reducible to $CH_2NH_2$. The reduction may be effected in a conventional manner, i.e., catalytic hydrogenation, lithium aluminum hydride, or electrolytic reduction.

When Q is a cyano group, Q is most conveniently reduced with a boron hydride, especially borane, or with a complex metal hydride such as lithium aluminum hydride, calcium borohydride, or sodium borohydride in the presence of aluminum chloride or of boron trifluoride. This reaction is typically conducted in an inert solvent such as ethyl ether, tetrahydrofuran or dioxane. Compounds wherein Q is a cyano group may also be reduced electrolytically.

The compound of formula I and its non-toxic acid addition salts can be used to treat diverse types of susceptible microbial infections. Furthermore, they are useful for preserving a wide variety of preparations including medicinal, veterinary, cosmetic and food preparations from microbial contamination by incorporating a stabilizing amount of the compound into the preparation in which the preservation is desired.

Susceptibility can be readily determined by standard in vivo and in vitro tests well known to the microbiologist. Genera of susceptible microorganisms include bacteria, fungi, protozoa and viruses. The compound of this invention also exhibits selective herbicidal activity in pre-emergence treatment.

Exemplifying susceptible bacterial microorganisms are *Staphylococcus aureus, Streptococcus pyogenes C., Bacillus subtillis, Escherichia coli* and *Pseudomonas aeruginosa.* Susceptible fungi include *Candida albicans, Trichophyton mentagrophytes* and *Saccharomyces cerevisiae.* Susceptible protozoal pathogens include *Trichomonas vaginalis* and *Entamoeba histolytica.* A susceptible virus is *Herpesvirus hominis* type 1.

Tables I to IX give the results of various in vitro and in vivo tests of 2-aminomethyl-3-(2,4-dichlorophenyl)indole against a variety of microorganisms including bacteria, fungi, protozoa and viruses and also report its toxicity and herbicidal activity. All the tests carried out and (when necessary) scored under standard conditions. "MIC" means "minimum inhibitory concentration."

Table I

| In vitro antibacterial activity of 2-aminomethyl-3-(2,4-dichlorophenyl)indole. Dilution in Mueller Hinton Agar pH 7.4. ||
|---|---|
| Organism | MIC (mcg/ml) |
| *Staphylococcus aureus* | |
| 209P | 3.0 |
| Wood | 3.0 |
| Ziegler | 0.8 |
| Gray | 3.0 |
| 59N | 3.0 |
| *Streptococcus pyogenes* | |
| C | 3.0 |
| 27 | 3.0 |
| Cruz | 0.8 |
| *Enterococcus 373* | 3.0 |
| 0928/72 | 3.0 |
| *Escherichia coli* | |
| 10536 | 3.0 |
| 1574-1 | 3.0 |
| 777 | 3.0 |

Table I-continued

*In vitro* antibacterial activity of 2-aminomethyl-3-(2,4-dichlorophenyl)indole. Dilution in Mueller Hinton Agar pH 7.4.

| Organism | MIC (mcg/ml) |
|---|---|
| 4195 | 3.0 |
| JR66 | 3.0 |
| *Klebsiella AD17* | 7.5 |
| AD22 | 3.0 |
| G3694 | 3.0 |
| 3020 | 3.0 |
| 121 | 7.5 |
| *Proteus mirabilis* Hard | 3.0 |
| Peras | 17.5 |
| *Proteus rettgeri mirabilis* | 17.5 |
| *Proteus vulgaris* Napol | 3.0 |
| *Proteus morganii* Valz | 17.5 |
| *Pseudomonas aeruginosa* | |
| 8709 | 7.5 |
| 762 | 17.5 |
| 130 | 7.5 |
| 138 | 17.5 |
| Trav. 1 | 17.5 |
| *Salmonella ent. 1* | 3.0 |
| $C_2$ Napo | 3.0 |
| B typhi | 3.0 |
| $C_1$ Oso | 3.0 |
| $C_2$ Cuban | 3.0 |

Table II

*In vitro* activity of 2-aminomethyl-3-(2,4-dichlorophenyl)indole against anaerobes in fluid Thioglycollate medium.

| Organism | MIC (mcg/ml) after | |
|---|---|---|
| | 48 hours | 72 hours |
| *Bacteroides melaninogenicus* | 3.0 | 3.0 |
| *Bacteroides fragilis* | 0.75 | 0.75 |
| *Bacteroides corrodens* | 0.75 | 3.0 |
| *Eubacterium lentum* | 3.0 | 3.0 |
| *Clostridium novyi* | 0.75 | 0.75 |
| *Clostridium septicum* | 0.75 | 0.75 |
| *Clostridium histolyticum* | 0.3 | 0.3 |
| *Peptostreptococcus* | 0.75 | 0.75 |
| *Corynebacterium acnes* 6921 | 0.3 | 0.3 |
| *Corynebacterium acnes* 6912 | 0.3 | 0.3 |
| *Corynebacterium acnes* 0922 | 0.3 | 0.3 |
| *Corynebacterium acnes* 0923 | 0.3 | 0.3 |

Table III

*In vitro* anti-Candida Activity of 2-aminomethyl-3-(2,4-dichlorophenyl)indole. Dilutions in Sabouraud's Dextrose Agar.

| *Candida albicans* | MIC (mcg/ml after 48 hours) |
|---|---|
| Burke | 37.5 |
| Lusk | 37.5 |
| Blunden | 37.5 |
| Fix | 37.5 |
| Collins | 37.5 |
| Merkel | 37.5 |
| 29 | 37.5 |
| Wisconsin | 37.5 |
| Sparks | 37.5 |
| Bevan | 37.5 |
| Newcomb | 17.5 |
| Kennedy 1 | 37.5 |
| Pannell | 17.5 |
| Atkisson | 37.5 |
| 1 | 37.5 |
| 2 | 37.5 |
| 3 | 37.5 |
| 4 | 17.5 |
| 5 | 17.5 |
| 6 | 37.5 |
| 8 | 37.5 |
| 9 | 37.5 |
| Burnside | 37.5 |
| Lehtman | 37.5 |
| Fulcher | 37.5 |
| Shurelli | 37.5 |
| Frazier | 37.5 |
| Boyer | 37.5 |
| Sherod | 37.5 |
| Bognay | 37.5 |
| Johnson | 37.5 |
| Gay | 37.5 |
| Tyner | 37.5 |
| Kennedy 2 | 37.5 |
| Bertrand | 37.5 |

Table III-continued

*In vitro* anti-Candida Activity of 2-aminomethyl-3-(2,4-dichlorophenyl)indole. Dilutions in Sabouraud's Dextrose Agar.

| *Candida albicans* | MIC (mcg/ml after 48 hours) |
|---|---|
| Hons | 37.5 |

Table IV

*In vitro* antifungal activity of 2-aminomethyl-3-(2,4-dichlorophenyl)indole against *Dermatophytes* and *Aspergillus*. Dilutions in Sabouraud's Dextrose Broth.

| Fungi | | MIC (mcg/ml) after 96 hours |
|---|---|---|
| *Trichophyton* | ascoides | 7.5 |
| | discoides | 7.5 |
| | ferrugineum | 7.5 |
| | gallinae | 17.5 |
| | megninii | 3.0 |
| | mentagrophytes A | 3.0 |
| | mentagrophytes B | 17.5 |
| | mentagrophytes C | 17.5 |
| | mentagrophytes Young | 3.0 |
| | mentagrophytes H377 | 7.5 |
| | rubrum Blehl | 3.0 |
| | rubrum 3 | 3.0 |
| | rubrum Haggerty | 3.0 |
| | rubrum 360 | 3.0 |
| | schoenleinii | 3.0 |
| | schoenleinii 2 | 3.0 |
| | soudenense | 7.5 |
| | tonsurans | 7.5 |
| *Tricoderm sp.* | | 3.0 |
| *Microsporum nanum* | | 3.0 |
| *Microsporum distortum* | | 3.0 |
| *Epidermophyton floccosum* | | 3.0 |
| *Aspergillus sp.* No. 3 | | 17.5 |
| *Aspergillus niger* 6275 | | 17.5 |

Table V

Acute toxicity of 2-aminomethyl-3-(2,4-dichlorophenyl)indole in mice.

| Route of Administration | Acute $LD_{50}$ (mg/kg) |
|---|---|
| I. P. | 85 |
| S. C. | 540 |
| Oral | about 700 |

Table VI

Effect of 2-aminomethyl-3-(2,4-dichlorophenyl)indole against topical *T. mentagrophytes* infections in guinea pigs.

| Concentration | Average No. of days to become negative | | Average sum of lesion scores | |
|---|---|---|---|---|
| | Cultures | Lesion | Days 1–5 | Days 1–10 |
| 1% | >22 | >22 | 12.6 | 34.2 |
| 4% | 6.6 | 9.2 | 11.6 | 15.2 |
| Untreated controls | >22 | >22 | 14.8 | 38.2 |

Table VII

*In vitro* anit-trichomonal activity of 2-aminomethyl-3-(2,4-dichlorophenyl)indole.

| Level to Produce | Minimal Level mcg/ml |
|---|---|
| 90% suppression | 28 |
| 50% suppression | 14 |

Table VIII

Viricidal activity of 2-aminomethyl-3-(2,4-dichlorophenyl)indole against *Herpesvirus hominis*, type 1. (HVH-1) Compounds were diluted in 0.1 N HCl, HVH-1 was added to the dilution, incubated at 37° C for 15 minutes and surviving virus determined by plaque assay.

| Concentration (mcg/ml.) | Surviving virus (PFU/ml) | % Survival |
|---|---|---|
| 40 | $1.3 \times 10^3$ | 0.2 |
| 20 | $1.9 \times 10^4$ | 2.3 |
| 10 | $7.8 \times 10^4$ | 9.3 |

PFU/ml = Plaqueforming units/ml.

Table IX

Herbicidal activity in pre-emergence treatment in paddy condition of 2-aminomethyl-3-(2,4-dichlorophenyl)indole against the weed *Cyperus difformis.*

| Rate (g/10a) | Activity |
|---|---|
| 1000 | +++ |

− not effective
+ slightly effective
++ moderately effective
+++ highly effective; plants are almost or completely dead
g/10a = grams/10 acres The invention, therefore, provides compositions containing, as an active ingredient, 2-aminomethyl-3-(2,4-dichlorophenyl)indole or an acid addition salt thereof, in association with a suitable carrier, excipient or diluent. In its function as active ingredient, the compound or salt thereof may be used to preserve the carrier from microbial contamination; for example, the carrier may be oil, paper, leather, photographic emulsion, canvas or rope. If the salt is non-toxic, the carrier may also be a food-stuff, food-additive or food-supplement, or a medicinal or cosmetic preparation. Such medicinal or cosmetic preparations may conveniently be in fluid form, e.g., lotions, creams, ointments, solutions, suspensions or aerosol preparations.

When used as preservatives, the 2-aminomethyl-3-(2,4-dichlorophenyl)indole or its salts are preferably incorporated into the composition to be preserved in an amount of 0.05 to 1% by weight, especially 0.1 to 0.5% by weight.

The compositions of the present invention may also be used as disinfectants and sanitizers. Particular uses include the disinfection and sanitization of floors, table tops, and other such surfaces, particularly in hospitals, clinics and nursing homes. Another use would be as a sterilizing agent to prevent the growth of pathogenic bacteria in the water for cut flowers and the soil of potted plants for hospitals, particularly intensive-care and burn wards patients highly susceptible to such bacteria.

The 2-aminomethyl-3-(2,4-dichlorophenyl)indole and its non-toxic acid addition salts can themselves be used in medicine as antimicrobial and antiviral agents and thus may be formulated as pharmaceutical compositions containing at least one said compound or salt together with a pharmaceutical carrier or excipient. Such a composition may, for example, be in the form of shaped products, in particular dosage units such as pills, tablets, capsules, dragees, lozenges or suppositories (especially vaginal suppositories). Alternatively, such compositions may be adapted for injection and therefore have as the carrier a sterile, pyrogen-free, injectable liquid. Injectable compositions will normally be in the form of dosage units; the various dosage units mentioned conveniently contain from 2 to 100 mg., preferably from 5 to 50 mg., of a compound of formula I or a non-toxic acid addition salt thereof.

Compositions for oral administration, other than dosage units mentioned above, may be exemplified by powders, granulates, solutions, suspensions, elixirs or aerosols. Compositions for topical application may be exemplified by ointments, creams, lotions, solutions, suspensions, aerosols, gels, shampoos, soaps or dusting powders. The compositions may be adapted in particular as opthalmic, otic or nasal preparations. Such compositions will normally be based upon standard carriers such as those selected from pharmaceutically acceptable vegetable oils, pharmaceutically acceptable polyalkylene glycols, isopropanol, gelatin, benzyl alcohol, gums, glycerol, petrolatum, preservatives, starch, sugars such as lactose, talc, magnesium stearate, aerosol propellants such as chlorofluoroalkanes, and coloring, flavoring, sweetening, thickening, suspending, dispersing, emulsifying, wetting, stabilizing and buffering agents.

The composition may also be in the form of an animal feed-stock, feed-additive or feed-supplement.

Compositions in which the active ingredient is 2-aminomethyl-3-(2,4-dichlorophenyl)indole or non-toxic acid addition salt thereof preferably contain from 0.5 to 10% thereof.

A suitable parenteral dosage range of 2-aminomethyl-3-(2,4-dichlorophenyl)indole or the non-toxic acid addition salts thereof is about 2 to 10 mg/kg per day. The 2-aminomethyl-3-(2,4-dichlorophenyl)indole and its non-toxic acid addition salts may be formulated into dosage forms as the sole active ingredient or used in association with other ingredients to extend the therapeutic spectrum.

When used as a herbicide, 2-aminomethyl-5-chloro-3-(2,4-dichlorophenyl)indole or its acid addition salts, may be applied to the ground in the pre-plant or pre-emergence treatment in a number of ways. The water-soluble salts may be sprayed simply as alcoholic/aqueous solutions. The compounds may also be deposited as dusts containing a powdered carrier such as talc, attaclay, etc. The compound itself can be applied as an emulsion with commercially available surface-active agents. Among the surface active agents which may be used are the sulfonated vegetable oils, sodium lauryl sulfate, Tween No. 20 (a polyalkylene ether alcohol), carbowax (polyethylene glycols of M. W. 1500 or more) and polyoxyethylene glycol monolaurate. Penetrants, sequestrants, mineral oils and co-solvents may also be included in the formulations.

The following examples describe in detail the compound and compositions illustrative of the present invention. It will be apparent to those skilled in the art that many modifications, both of materials and methods, may be practiced without departing from the purpose and intent of this disclosure.

Example 1

2-Aminomethyl-5-chloro-3-(2,4-dichlorophenyl)indole

Step A:

N-[2-(2,4-dichlorobenzoyl)-4-chloro]phenylglycinonitrile

Mix together 2-amino-2',4',5-trichlorobenzophenone (5 g.), potassium cyanide (3.25 g.), and paraformaldehyde (2.5 g.). Then add 12.5 ml. of acetic acid saturated with hydrogen chloride and 12.5 ml. of acetic acid. Keep the temperature below 70° C for several minutes and then boil under reflux for 5 minutes. Cool and pour onto ice water. Collect the precipitate and extract with chloroform. Treat this solution with sodium carbonate solution and then water and dry using $MgSO_4$. Evaporate to yield the title compound. Recrystallize from methylene chloride-petroleum ether; m.p. 166°–167° C.

Step B:

5-Chloro-3-(2,4-dichlorophenyl)indole-2-carbonitrile

Dissolve the glycinonitrile of Step A (40 g.) in 175 ml. of dry tetrahydrofuran. Add 50 ml. of trifluoroacetic anhydride. Boil under reflux overnight. Remove the solvent under nitrogen. Add more solvent and remove twice. Dissolve the crystalline residue in tetrahydrofuran, and treat with 20 g. of 57% sodium hydride in mineral oil. Boil under reflux for 30 minutes and pour into ice water. Stir and collect the solid. Wash with water, dry and wash with petroleum ether. Crystallize from methylene chloride-petroleum ether to obtain the title compound: m.p. 181°–182° C.

Step C:
2-Aminomethyl-5-chloro-3-(2,4-dichlorophenyl)indole

Dissolve the nitrile (22 g.) of step B in a mixture of 137 ml. of 1 molar borane in tetrahydrofuran and 100 ml. of tetrahydrofuran and stir for 4 hours. Boil under reflux for 0.5 hour, cool and add 5 N hydrochloric acid. Boil under reflux for 1 hour and pour onto a mixture of ice and 10% ammonia. Extract with chloroform, wash and dry using MgSO$_4$. Evaporate to yield the title compound. Crystallize from ether-petroleum ether to obtain the analytical sample: m.p. 179°–180° C. To prepare the hydrochloride salt, dissolve this material in ethanol, add concentrated hydrochloric acid, collect and dry the material: m.p. 226°–228° C.

Example 2

| Topical Cream | Per kg. |
|---|---|
| 2-Aminomethyl-5-chloro-3-(2,4-dichlorophenyl)indole | 10 g. - 100 g. |
| Ethoxylated Cetyl/Stearyl Alcohol | 20 g. |
| Cetyl Alcohol | 35 g. |
| Stearyl Alcohol | 35 g. |
| Petrolatum | 200 g. |
| Mineral Oil | 50 g. |
| Buffers, Sufficient | — |
| Preservatives, Sufficient | — |
| Purified water to make | 1.0 kg. |

Add the cetyl alcohol, stearyl alcohol, ethoxylated cetyl/stearyl alcohol, petrolatum and mineral oil to a suitable mixing vessel. Heat to 80° C to melt. Mix. Add the preservatives, buffers and 2-aminomethyl-5-chloro-3-(2,4-dichlorophenyl)indole in approximately 95% of the purified water heated to 80° C in a suitable mixing vessel. Mix. Add the melted wax phase to the aqueous phase and mix while cooling to about 40° C. Add sufficient purified water to make 1 kg. Mix until cool.

Example 3

| Topical Ointment | Per kg. |
|---|---|
| 2-Aminomethyl-5-chloro-3-(2,4-dichlorophenyl)indole | 10 g. - 100 g. |
| White petrolatum, to make | 1.0 kg. |

Melt and heat the petrolatum to 50° C in a suitable mixing vessel. Remove a portion of the melted petrolatum and make therewith a slurry of the 2-aminomethyl-5-chloro-3-(2,4-dichlorophenyl)indole. Pass the slurry through a suitable colloid mill and mill until a uniform dispersion is obtained. Add the milled slurry to the remainder of the melted petrolatum and mix until cool.

Example 4

| Otic Suspension | mg/ml |
|---|---|
| 2-Aminomethyl-5-chloro-3-(2,4-dichlorophenyl)indole | 5–10 |
| Cetylpyridinium Chloride, NF | 0.20 |
| Glyceryl Triacetate | 880.0 |
| Polyethylene Glycol 200 q.s. ad | 1.0 ml. |

Melt and heat the petrolatum to 50° C in a suitable mixing vessel. Remove a portion of the melted petrolatum and make therewith a slurry of the 2-aminomethyl-5-chloro-3-(2,4-dichlorophenyl)indole. Pass the slurry through a suitable colloid mill until a uniform dispersion is obtained. Add the milled slurry to the remainder of the melted petrolatum and mix until cool.

Example 5

| Vaginal Tablets | mg/tablet | mg/tablet |
|---|---|---|
| 2-Aminomethyl-5-chloro-3-(2,4-dichlorophenyl)indole | 10.0 | 5.0 |
| Lactose Hydrous, Impalpable powder USP | 772.0 | 777.0 |
| Sodium Lauryl Sulfate | 20.0 | 20.0 |
| Polyvinylpyrrolidone | 40.0 | 40.0 |
| Corn Starch, Food Grade | 150.0 | 150.0 |
| Magnesium Stearate | 8.0 | 8.0 |
| | 1000 mg. | 1000 mg. |

Example 6

| Intramuscular or Subcutaneous Oil Injection | mg/ml |
|---|---|
| 2-Aminomethyl-5-chloro-3-(2,4-dichlorophenyl)indole | 20–50 |
| Aluminum Monostearate, USP | 20.0 |
| Sesame Oil, Heat treated, USP q. s. ad | 1.0 ml |

Example 7

| Topical Cream | Per kg. |
|---|---|
| 2-Aminomethyl-5-chloro-3-(2,4-dichlorophenyl)indole hydrochloride | 10 g.–100 g. |
| Stearic acid | 60 g. |
| Propylene Glycol Monostearate | 100 g. |
| Isopropyl Myristate | 80 g. |
| Polyoxyethylene (20) Sorbitan Monopalmitate | 60 g. |
| Sorbitan Solution | 20 g. |
| Buffers, Sufficient | — |
| Preservatives, Sufficient | — |
| Purified Water to make | 1.0 kg. |

Add the stearic acid, propylene glycol monostearate, isopropyl myristate and polyoxyethylene (20) sorbitan monopalmitate to a suitable mixing vesse. Heat to 80° C to melt. Mix.

Examples 8 to 10 illustrate compositions preserved with 2-aminomethyl-5-chloro-3-(2,4-dichlorophenyl)indole.

Example 8

| Lotion | mg/ml |
|---|---|
| Betamethasone Valerate | 1.22 |
| 2-aminomethyl-5-chloro-3-(2,4-dichlorophenyl)indole | 1.00 |
| Mineral Oil USP | 19.50 |
| Diethylene Glycol Monostearate S.E. | 6.50 |
| Cetostearyl Alcohol | 6.50 |
| Lanbritol Wax | 9.30 |
| Glycerin, USP | 50.00 |
| Isopropanol | 65.00 |
| Citric Acid | 0.08 |
| Purified Water, USP to make | 1.00 ml |

Example 9

| Intramuscular or Intravenous Solution | mg/ml |
|---|---|
| Gentamicin (charged as sulfate) | 40.0 |
| Sodium Bisulfite, USP | 3.2 |
| Disodium Edetate, USP | 0.1 |
| 2-aminomethyl-5-chloro-3-(2,4-dichlorophenyl)indole (charged as the hydrochloride salt) | 1.3 |
| Water for Injection, q.s. ad | 1.0 ml |

Example 10

| Aerosol Concentrate | mg/g |
| --- | --- |
| Megalomicin A Phosphate | 20.0 |
| 2-aminomethyl-5-chloro-3-(2,4-dichlorophenyl)indole | 1.0 |
| Liquid Absorption Base | 90.0 |
| Stearic Acid | 25.0 |
| Glyceryl Monostearate | 25.0 |
| Isopropyl Myristate | 50.0 |
| Glycerol, USP | 100.0 |
| Alcohol SD 40 | 80.0 |
| Triethanolamine | 10.0 |
| Purified Water USP to make | 1.0 g |

This composition is packaged into an aerosol container with standard polyfluoroalkane propellant mixtures.

What is claimed is:

1. The compound which is 2-aminomethyl-5-chloro-3-(2,4-dichlorophenyl)indole and the acid addition salts thereof.

UNITED STATES PATENT OFFICE
CERTIFICATE OF CORRECTION

Patent No. 4,070,369   Dated January 24, 1978

Inventor(s) Martin Steinman

It is certified that error appears in the above-identified patent and that said Letters Patent are hereby corrected as shown below:

In Column 4, line 52, "In vitro anit-" should read --- In vitro anti- ---.  Column 8, line 23, "20-50" should read --- 10-50 ---.

Signed and Sealed this

Thirty-first Day of October 1978

[SEAL]

Attest:

RUTH C. MASON
Attesting Officer

DONALD W. BANNER
Commissioner of Patents and Trademarks